(12) United States Patent
Varma et al.

(10) Patent No.: US 10,189,708 B2
(45) Date of Patent: Jan. 29, 2019

(54) RUTHENIUM ON CHITOSAN (CHRU): CONCERTED CATALYSIS FOR WATER SPLITTING AND REDUCTION

(71) Applicant: The United States of America as Represented by the Administrator of the U.S. Environmental Protection Agency, Washington, DC (US)

(72) Inventors: Rajender S. Varma, Cincinnati, OH (US); Nasir Baig, Cincinnati, OH (US); Mallikarjuna Nadagouda, Cincinnati, OH (US)

(73) Assignee: The United States of America as represented by the U.S. Environmental Protection Agency, Washington, DC (US)

( * ) Notice: Subject to any disclaimer, the term of this patent is extended or adjusted under 35 U.S.C. 154(b) by 343 days.

(21) Appl. No.: 15/240,396

(22) Filed: Aug. 18, 2016

(65) Prior Publication Data
US 2018/0050906 A1    Feb. 22, 2018

(51) Int. Cl.
| | | |
|---|---|---|
| *B01J 19/12* | (2006.01) | |
| *C01B 3/04* | (2006.01) | |
| *B01J 23/44* | (2006.01) | |
| *B01J 23/46* | (2006.01) | |
| *B01J 31/06* | (2006.01) | |
| *B01J 35/00* | (2006.01) | |
| *B01J 37/00* | (2006.01) | |
| *B01J 37/02* | (2006.01) | |

(Continued)

(52) U.S. Cl.
CPC ............ *C01B 3/042* (2013.01); *B01J 19/126* (2013.01); *B01J 23/44* (2013.01); *B01J 23/462* (2013.01); *B01J 23/745* (2013.01); *B01J 31/061* (2013.01); *B01J 35/002* (2013.01); *B01J 37/009* (2013.01); *B01J 37/0236* (2013.01); *B01J 37/035* (2013.01); *C01B 13/0207* (2013.01); *C07C 209/365* (2013.01); *C01B 2203/0277* (2013.01)

(58) Field of Classification Search
CPC ............... C01B 3/042; C01B 13/0207; C01B 2203/0277; B01J 23/44; B01J 23/745; B01J 35/002; B01J 37/009; B01J 37/0236; B01J 31/061; B01J 37/035; B01J 23/462; C07C 209/365
USPC ............. 204/157.43, 257.52, 157.81, 157.86
See application file for complete search history.

(56) References Cited

U.S. PATENT DOCUMENTS 4,274,980 A * 6/1981 Arena .................... B01J 31/061
                                                                    502/159
4,382,846 A * 5/1983 Gratzel ................... C01B 3/042
                                                                    204/157.5

(Continued)

OTHER PUBLICATIONS

Al-Shaal et al, "Microwave-assisted reduction of levulinic acid with alcohols producing γ-valerolactone in the presence of a Ru/C catalyst," Catalysis Communications 75 (2016) 65-68 (Year: 2016).*

(Continued)

*Primary Examiner* — Nicholas A Smith
*Assistant Examiner* — Colleen M Raphael
(74) *Attorney, Agent, or Firm* — Stein IP, LLC

(57) ABSTRACT

A process and catalyst for the in situ generation of hydrogen via the microwave irradiation of a ruthenium chitosan composite catalyst has enabled the convenient reduction of nitro compounds in aqueous medium.

16 Claims, 20 Drawing Sheets

Chitosan-Ru (ChRu) composite

(51) Int. Cl.
*B01J 37/03* (2006.01)
*C01B 13/02* (2006.01)
*B01J 23/745* (2006.01)
*C07C 209/36* (2006.01)
*C07C 211/52* (2006.01)

(56) References Cited

U.S. PATENT DOCUMENTS

| | | | | | |
|---|---|---|---|---|---|
| 4,637,867 | A | * | 1/1987 | Herbst, Jr. | C01B 3/042 204/157.52 |
| 5,262,023 | A | * | 11/1993 | Sayama | C01B 3/042 204/157.5 |
| 5,399,993 | A | * | 3/1995 | Kleinberg | C01C 3/02 204/157.43 |
| 5,650,051 | A | * | 7/1997 | Wada | B01J 7/02 204/157.52 |
| 2008/0292536 | A1 | * | 11/2008 | Demuth | C01B 3/042 423/580.1 |
| 2008/0314435 | A1 | * | 12/2008 | He | B82Y 20/00 136/246 |
| 2011/0220484 | A1 | * | 9/2011 | Obenland | B01J 23/26 204/157.5 |
| 2012/0247946 | A1 | * | 10/2012 | Obenland | B01J 23/888 204/157.5 |
| 2013/0252808 | A1 | * | 9/2013 | Yamazaki | C07C 29/159 502/303 |
| 2016/0060769 | A1 | * | 3/2016 | McDonald | C25B 1/003 205/632 |
| 2016/0361713 | A1 | * | 12/2016 | Pastori | B01J 31/38 |

OTHER PUBLICATIONS

Takahashi et al, "Hydrogen transfer type oxidation of alcohols by rhodium and ruthenium catalyst under microwave irradiation," Tetrahedron Letters 44 (2003) 9201-9203 (Year: 2003).*
C. Oliver Kappe, "*Reply to the Correspondence on Microwave Effects in Organic Synthesis*", 2013, pp. 2-7.
Gregory B. Dudley, et al., "*Correspondence on Microwave Effects in Organic Synthesis*", 2013, pp. 2-8.
R.B. Nasir Baig, et al., "*N-Allylation of allyl acetates using chitosanimmobilized Palladium*", 2012, pp. 1-3.
Takashi Hisatomi, et al., "*Recent advances in semiconductors for photocatalytic and photoelectrochemical water splitting*", Jan. 13, 2014, pp. 7520-7535.
Akihiko Kudo, et al., "*Heterogeneous photocatalyst materials for water splitting*", Nov. 18, 2008, pp. 253-279.
Javier J. Concepcion, et al., "*Making Oxygen with Ruthenium Complexes*", Dec. 2009, pp. 1954-1965.
Sophie Romain, et al., "*Oxygen-Oxygen Bond Formation Pathways Promoted by Ruthenium Complexes*", Dec. 2009, pp. 1944-1953.
Gareth S. Parkinson, et al., "*Room Temperature Water Splitting at the Surface of Magnetite*", Jul. 8, 2011, pp. 12650-12655.
Ricardo H. Gonçalves, et al., "*Magnetite Colloidal Nanocrystals: A Facile Pathway to Prepare Mesoporous Hematite Thin Films for Photoelectrochemical Water Splitting*", Mar. 28, 2011, pp. 6012-6019.
Masanobu Higashi, et al., "*Highly Stable Water Splitting on Oxynitride TaON Photoanode System under Visible Light Irradiation*", Apr. 10, 2012, pp. 6968-6971.
Matthew T. Mayer, et al., "*Hematite/Si Nanowire Dual-Absorber System for Photoelectrochemical Water Splitting at Low Applied Potentials*", Jul. 16, 2012, pp. 12406-12409.
J. Cohen, et al., "*Molecular dynamics and experimental investigation of H2 and O2 diffusion in [Fe]-hydrogenase*", Sep. 30, 2004, pp. 80-82.
Alexander S. Fedorov, et al., "*Continuous Hydrogen Photoproduction by Chlamydomonas reinhardtii*", 2005, pp. 403-412.
Gopal Sirasani, et al., "*A Biocompatible Alkene Hydrogenation Merges Organic Synthesis with Microbial Metabolism*", 2014, pp. 7785-7788.
László Vigh, et al., "*The primary signal in the biological perception of temperature: Pd-catalyzed hydrogenation of membrane lipids stimulated the expression of the desA gene in Synechocystis PCC6803*" Jun. 28, 1993, pp. 9090-9094.
Xin-Hao Li, et al., "*Mesoporous g-C3N4 nanorods as multifunctional supports of ultrafine metal nanoparticles: hydrogen generation from water and reduction of nitrophenol with tandem catalysis in one step*", Mar. 28, 2012, pp. 2170-2174.
Khurram Saleem Joya, et al., "*Water-Splitting Catalysis and Solar Fuel Devices: Artificial Leaves on the Move*", 2013, pp. 10426-10437.
R. B. Nasir Baig, et al., "*Magnetically retrievable catalysts for organic synthesis*", Nov. 7, 2012, pp. 752-770.
R. B. Nasir Baig, et al., "*Copper on chitosan: a recyclable heterogeneous catalyst for azide-alkyne cycloaddition reactions in water*", May 1, 2013, pp. 1839-1843.
R. B. Nasir Baig, et al., "*Ruthenium on chitosan: a recyclable heterogeneous catalyst for aqueous hydration of nitriles to amides*", Dec. 19, 2013, pp. 2122-2127.
Xinzheng Yang, et al., "*Mechanism of Water Splitting and Oxygen-Oxygen Bond Formation by a Mononuclear Ruthenium Complex*", 2010, pp. 120-130.
Michael J. Krische, et al., "*Hydrogenation and Transfer Hydrogenation*", Dec. 2007.
Iván Sorribes, et al., "*Chemoselective Transfer Hydrogenation to Nitroarenes Mediated by Cubane-Type Mo3S4 Cluster Catalysts*", Jun. 18, 2012, pp. 7794-7798.
David Cantillo, et al., "*In Situ Generated Iron Oxide Nanocrystals as Efficient and Selective Catalysts for the Reduction of Nitroarenes using a Continuous Flow Method*", Sep. 5, 2012, pp. 10190-10193.
Lin He, et al., "*Efficient and Selective Room-Temperature Gold-Catalyzed Reduction of Nitro Compounds with CO and $H_2O$ as the Hydrogen Source*", Nov. 17, 2009, pp. 9538-9541.

* cited by examiner

Chitosan-Ru (ChRu) composite

Sealed microwave tube

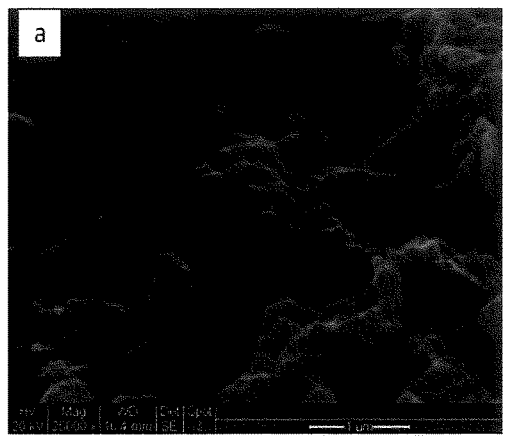
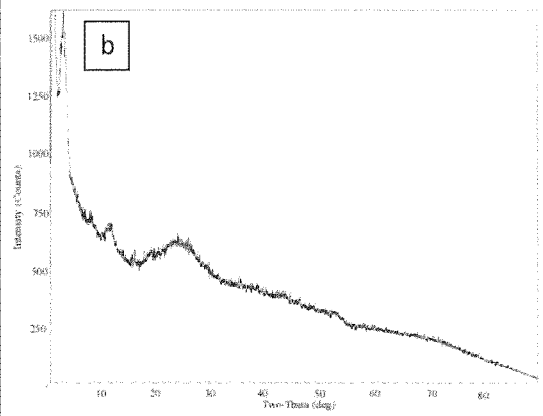
FIG. 3(a)  FIG. 3(b)
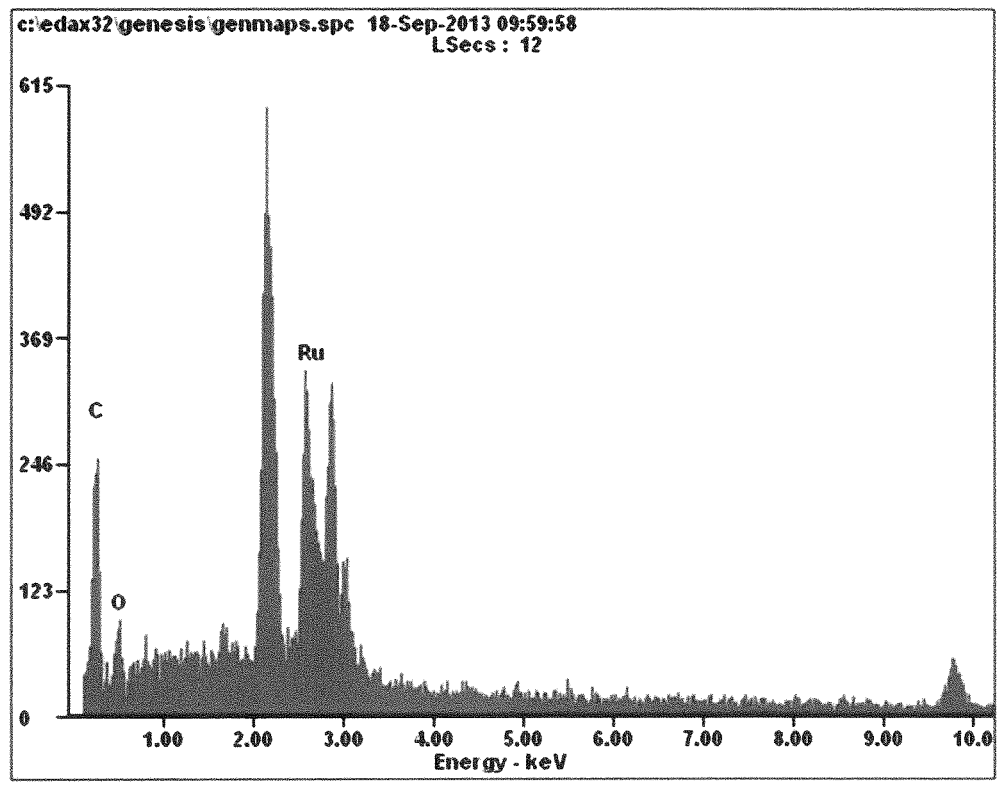
FIG. 3(c)

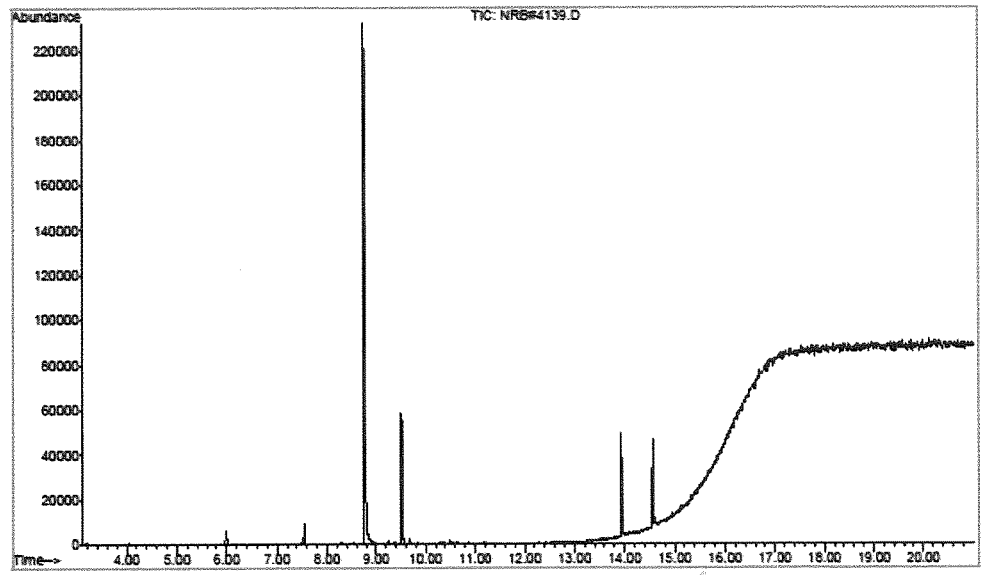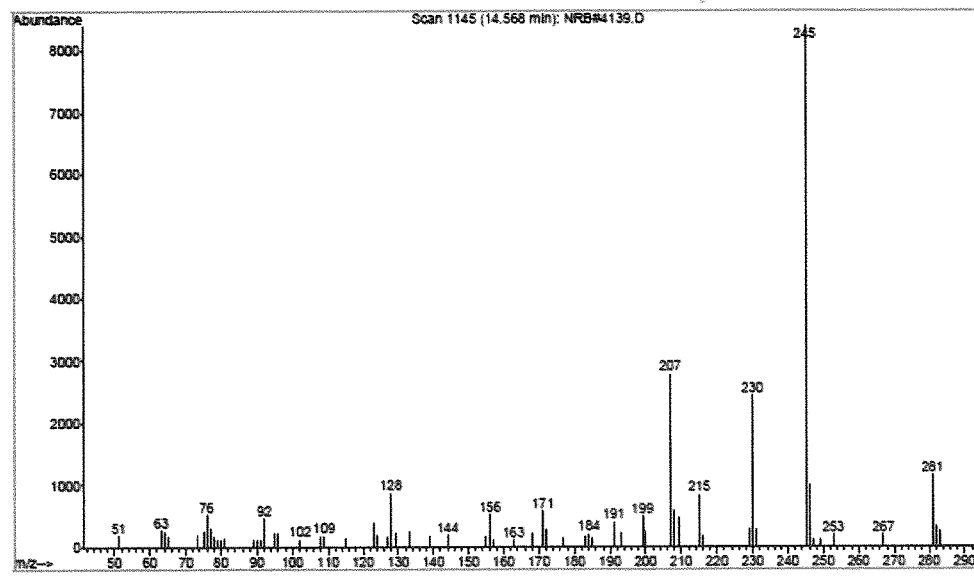
FIG. 5

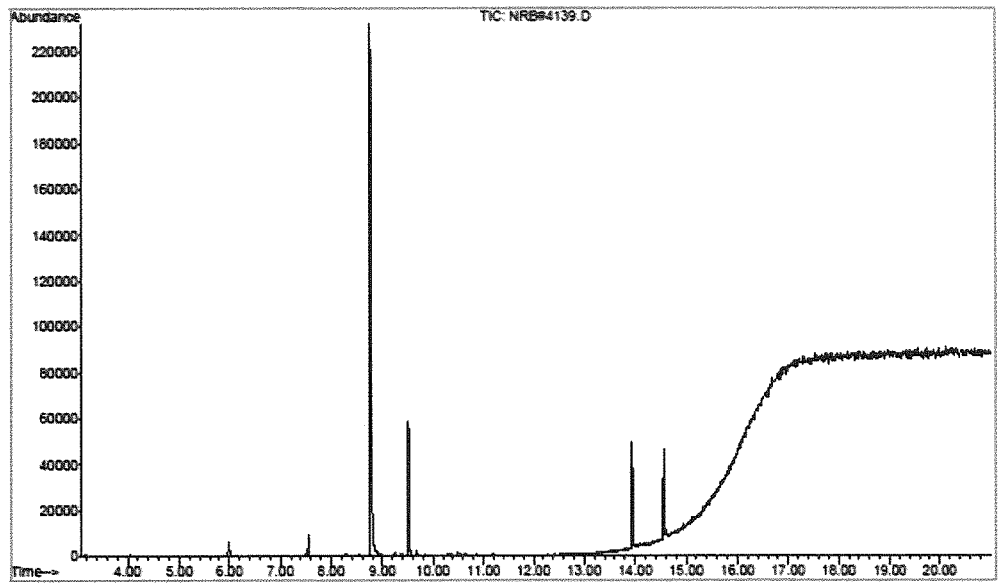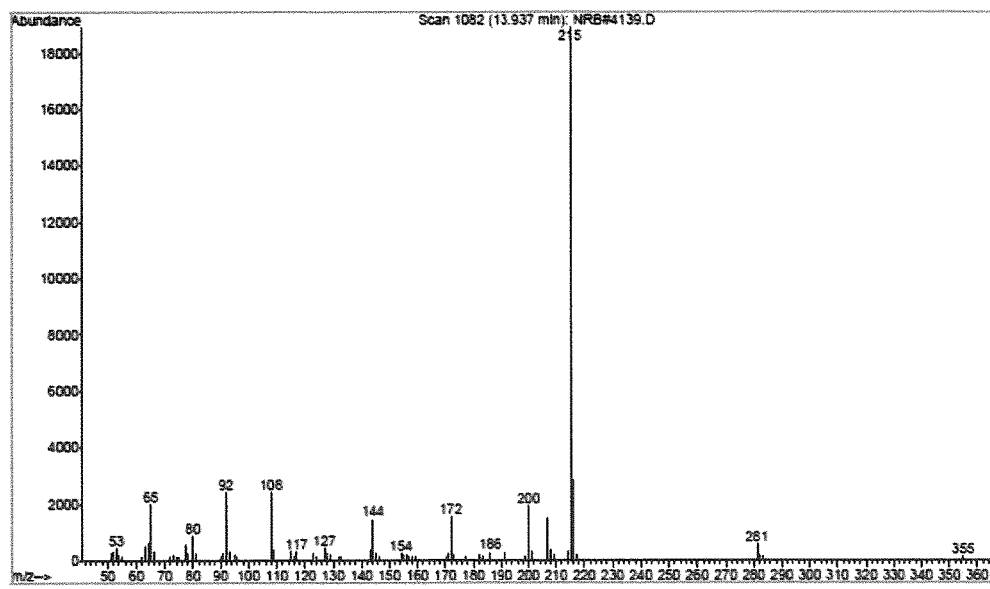
FIG. 6

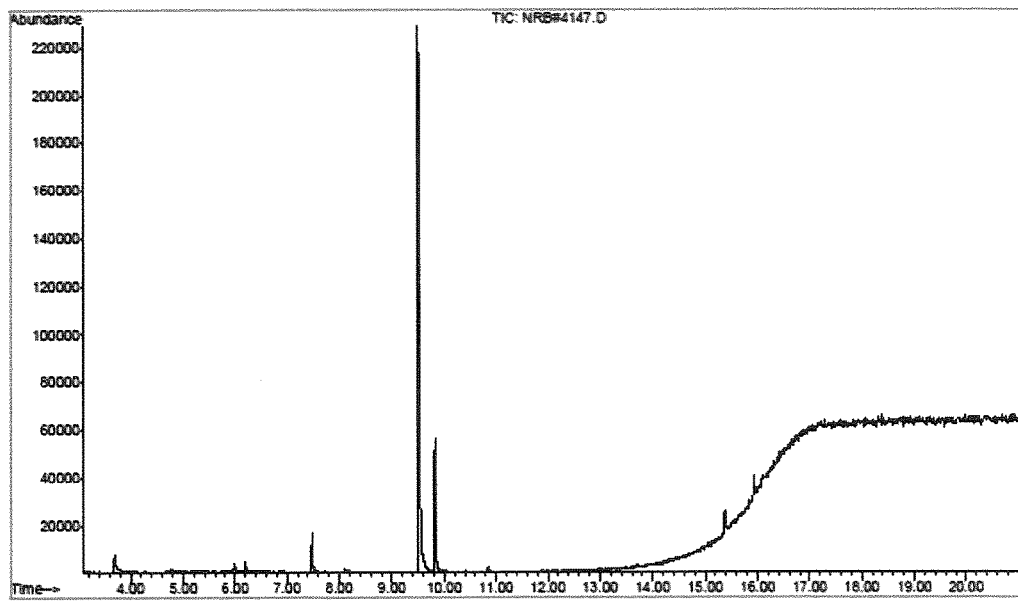
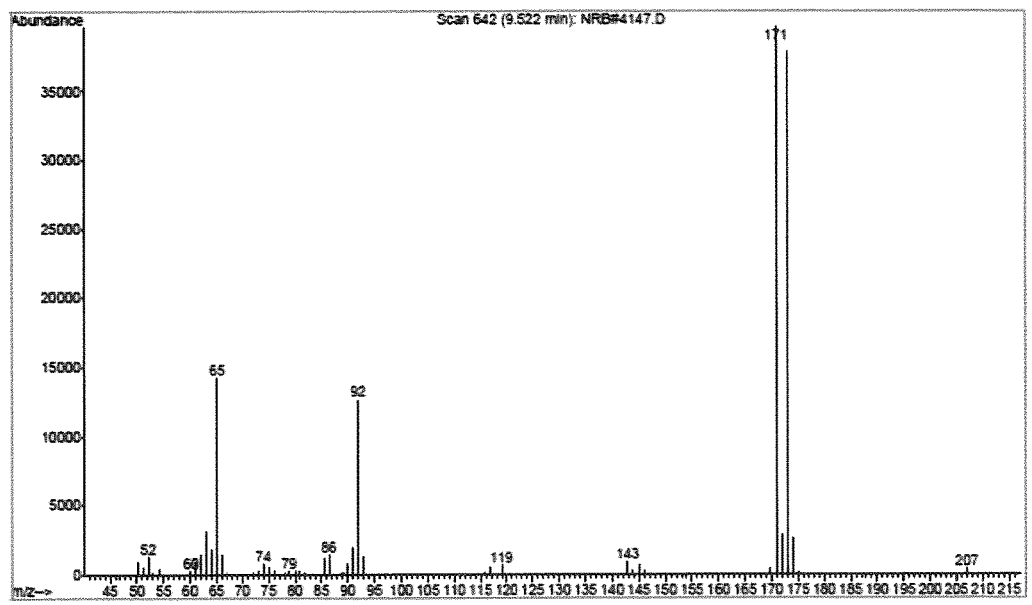
FIG. 7

```
Data File D:\DATA\NASIR\NASIR000463.D
Sample Name: NRB#4157-3

===============================================================================
Acq. Operator   : Nasir
Acq. Instrument : Instrument 1                    Location : Vial 1
Injection Date  : 14-Jun-13, 11:04:16                  Inj :  1
                                                Inj Volume : Manually
Acq. Method     : C:\CHEM32\1\METHODS\LANDFILL GAS TCD MAR2011.M
Last changed    : 6/14/2013 11:03:07 AM by Nasir
Analysis Method : C:\CHEM32\1\METHODS\LANDFILL GAS TCD MAR2011.M
Last changed    : 6/14/2013 11:11:16 AM by Nasir
Method Info     : Method for Landfill gases - CH4, CO2, CO, H2, N2, O2 Using Porapack N, Mol
                  Sieve, TCD - Steve Musson
```

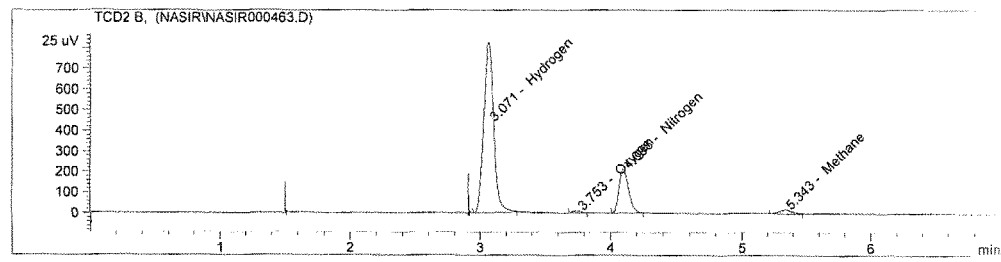

```
===============================================================================
                        Normalized Percent Report
===============================================================================

Sorted By           :      Signal
Calib. Data Modified :     Thursday, January 12, 2012 10:19:23 AM
Multiplier          :      1.0000
Dilution            :      1.0000
Use Multiplier & Dilution Factor with ISTDs Signal 1: TCD2 B, RetTime Type    Area       Amt/Area      Norm    Grp  Name
 [min]          [25 uV*s]                 %
-------|------|----------|------------|----------|--|--------------------
  2.497            -            -           -         Carbon Dioxide
  3.071 BB   4454.34131  4.83147e-3   27.793720      Hydrogen
  3.753 BV     43.57506  3.50659e-2    1.973363      Oxygen
  4.098 BB   1085.96875  4.84985e-2   68.018808      Nitrogen
  5.343 BV    128.70334  1.33206e-2    2.214109      Methane Totals :                              100.000000

2 Warnings or Errors :

Warning : Calibration warnings (see calibration table listing)
Warning : Calibrated compound(s) not found ===============================================================================
                            * End of Report *

Instrument 1 6/14/2013 11:11:25 AM Nasir                              Page   1 of 1
```

FIG. 8

```
Data File D:\DATA\NASIR\NASIR000462.D
Sample Name: NRB#4160
============================================================================
Acq. Operator    : Nasir
Acq. Instrument  : Instrument 1                    Location : Vial 1
Injection Date   : 14-Jun-13, 10:55:56                  Inj : 1
                                                 Inj Volume : Manually
Acq. Method      : C:\CHEM32\1\METHODS\LANDFILL GAS TCD MAR2011.M
Last changed     : 6/14/2013 10:53:26 AM by Nasir
Analysis Method  : C:\CHEM32\1\METHODS\LANDFILL GAS TCD MAR2011.M
Last changed     : 6/14/2013 11:02:56 AM by Nasir
Method Info      : Method for Landfill gases - CH4, CO2, CO, H2, N2, O2 Using Porapack N, Mol
                   Sieve, TCD - Steve Musson
```

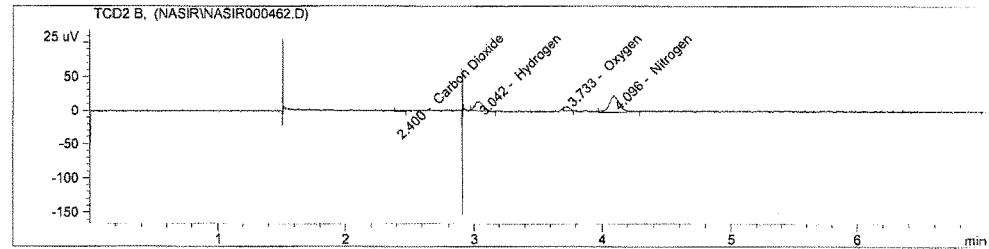

```
============================================================================
                         Normalized Percent Report
============================================================================

Sorted By             :    Signal
Calib. Data Modified  :    Thursday, January 12, 2012 10:19:23 AM
Multiplier            :    1.0000
Dilution              :    1.0000
Use Multiplier & Dilution Factor with ISTDs Signal 1: TCD2 B, RetTime Type     Area      Amt/Area       Norm   Grp   Name
 [min]          [25 uV*s]                   %
-------|------|-----------|----------|----------|--|--------------
  2.400 VV      6.80996  4.42418e-2    3.833679        Carbon Dioxide
  3.042 BV     67.58522  4.83147e-3    4.154983        Hydrogen
  3.733 VB     19.34842  3.50659e-2    8.633141        Oxygen
  4.096 VB    135.10970  4.84985e-2   83.378196        Nitrogen
  5.114           -          -            -            Methane Totals :                              100.000000

2 Warnings or Errors :

Warning : Calibration warnings (see calibration table listing)
Warning : Calibrated compound(s) not found ============================================================================
                            * End of Report *
```

Instrument 1  6/14/2013 11:03:04 AM Nasir                              Page 1 of 1

FIG. 9

```
Data File D:\DATA\NASIR\NASIR000472.D
Sample Name: NRB#4163

===============================================================================
Acq. Operator   : Nasir
Acq. Instrument : Instrument 1                  Location : Vial 1
Injection Date  : 14-Jun-13, 12:18:54                Inj : 1
                                            Inj Volume : Manually
Acq. Method     : C:\CHEM32\1\METHODS\LANDFILL GAS TCD MAR2011.M
Last changed    : 6/14/2013 12:18:01 PM by Nasir
Analysis Method : C:\CHEM32\1\METHODS\LANDFILL GAS TCD MAR2011.M
Last changed    : 6/14/2013 12:25:54 PM by Nasir
Method Info     : Method for Landfill gases - CH4, CO2, CO, H2, N2, O2 Using Porapack N, Mol
                  Sieve, TCD - Steve Musson
```

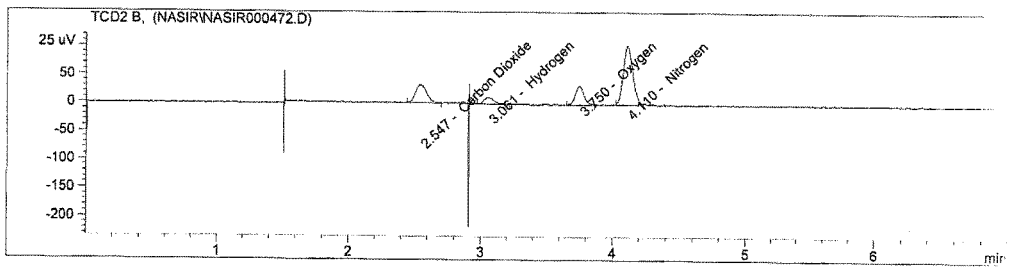

```
===============================================================================
                         Normalized Percent Report
===============================================================================

Sorted By            :    Signal
Calib. Data Modified :    Thursday, January 12, 2012 10:19:23 AM
Multiplier           :    1.0000
Dilution             :    1.0000
Use Multiplier & Dilution Factor with ISTDs Signal 1: TCD2 B, RetTime Type   Area       Amt/Area     Norm    Grp  Name
 [min]        [25 uV*s]                  %
-------|------|----------|----------|----------|---|-------------------
 2.547  BB    191.11461  4.42418e-2  21.277983      Carbon Dioxide
 3.061  BV     65.38754  4.83147e-3   0.795020      Hydrogen
 3.750  VB    153.32578  3.50659e-2  13.530192      Oxygen
 4.110  BV    527.63409  4.84985e-2  64.396806      Nitrogen
 5.114          -            -           -          Methane Totals :                             100.000000

2 Warnings or Errors :

Warning : Calibration warnings (see calibration table listing)
Warning : Calibrated compound(s) not found ===============================================================================
                           * End of Report *
```

Instrument 1 6/14/2013 12:26:03 PM Nasir                        Page  1 of 1

FIG. 10

```
Data File D:\DATA\NASIR\NASIR000473.D
Sample Name: NRB#4162
================================================================
Acq. Operator   : Nasir
Acq. Instrument : Instrument 1                Location : Vial 1
Injection Date  : 14-Jun-13, 12:27:31              Inj : 1
                                        Inj Volume : Manually
Acq. Method     : C:\CHEM32\1\METHODS\LANDFILL GAS TCD MAR2011.M
Last changed    : 6/14/2013 12:26:05 PM by Nasir
Analysis Method : C:\CHEM32\1\METHODS\LANDFILL GAS TCD MAR2011.M
Last changed    : 6/14/2013 12:34:31 PM by Nasir
Method Info     : Method for Landfill gases - CH4, CO2, CO, H2, N2, O2 Using Porapack N, Mol
                  Sieve, TCD - Steve Musson
```

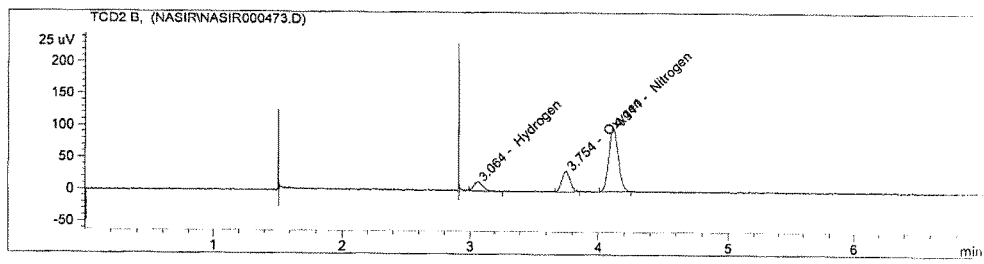

```
                     Normalized Percent Report
================================================================

Sorted By            :   Signal
Calib. Data Modified :   Thursday, January 12, 2012 10:19:23 AM
Multiplier           :   1.0000
Dilution             :   1.0000
Use Multiplier & Dilution Factor with ISTDs Signal 1: TCD2 B, RetTime Type    Area        Amt/Area     Norm    Grp  Name
 [min]         [25 uV*s]                  %
-------|------|-----------|------------|---------|--|-------------
 2.497    -        -           -           -          Carbon Dioxide
 3.064  VB     75.59394  4.83147e-3    1.225395       Hydrogen
 3.754  BV    144.85381  3.50659e-2   17.042162       Oxygen
 4.111  BB    502.29285  4.84985e-2   81.732443       Nitrogen
 5.114    -        -           -           -          Methane Totals :                              100.000000

2 Warnings or Errors :

Warning : Calibration warnings (see calibration table listing)
Warning : Calibrated compound(s) not found ================================================================
                         * End of Report *
```

Instrument 1 6/14/2013 12:34:40 PM Nasir                   Page 1 of 1

FIG. 11

```
Data File D:\DATA\NASIR\NASIR000465.D
Sample Name: NRB#4158-2
==========================================================================
Acq. Operator   : Nasir
Acq. Instrument : Instrument 1                     Location : Vial 1
Injection Date  : 14-Jun-13, 11:21:16              Inj :   1
                                                 Inj Volume : Manually
Acq. Method     : C:\CHEM32\1\METHODS\LANDFILL GAS TCD MAR2011.M
Last changed    : 6/14/2013 11:20:22 AM by Nasir
Analysis Method : C:\CHEM32\1\METHODS\LANDFILL GAS TCD MAR2011.M
Last changed    : 6/14/2013 11:28:16 AM by Nasir
Method Info     : Method for Landfill gases - CH4, CO2, CO, H2, N2, O2 Using Porapack N, Mol
                  Sieve, TCD - Steve Musson
```

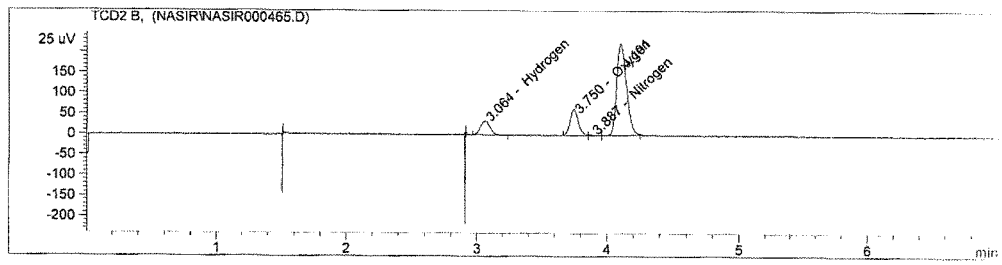

```
                        Normalized Percent Report
==========================================================================

Sorted By              :    Signal
Calib. Data Modified   :    Thursday, January 12, 2012 10:19:23 AM
Multiplier             :    1.0000
Dilution               :    1.0000
Use Multiplier & Dilution Factor with ISTDs Signal 1: TCD2 B, RetTime Type   Area       Amt/Area       Norm     Grp  Name
 [min]        [25 uV*s]                   %
-------|------|----------|------------|----------|--|------------------
  2.497         -             -            -          Carbon Dioxide
  3.064 BB   170.74980   4.83147e-3    7.396285       Hydrogen
  3.750 BV   283.68079   3.50659e-2   89.184455       Oxygen
  3.887 VV     7.86376   4.84985e-2    3.419260       Nitrogen
  5.114         -             -            -          Methane Totals :                               100.000000

2 Warnings or Errors :

Warning : Calibration warnings (see calibration table listing)
Warning : Calibrated compound(s) not found ==========================================================================
                          * End of Report *

Instrument 1 6/14/2013 11:28:25 AM Nasir                        Page  1 of 1
```

FIG. 12

```
Data File D:\DATA\NASIR\NASIR000461.D
Sample Name: NRB#4159-2
================================================================
Acq. Operator   : Nasir
Acq. Instrument : Instrument 1                Location : Vial 1
Injection Date  : 14-Jun-13, 10:46:14             Inj : 1
                                           Inj Volume : Manually
Acq. Method     : C:\CHEM32\1\METHODS\LANDFILL GAS TCD MAR2011.M
Last changed    : 6/14/2013 10:40:56 AM by Nasir
Analysis Method : C:\CHEM32\1\METHODS\LANDFILL GAS TCD MAR2011.M
Last changed    : 6/14/2013 10:53:14 AM by Nasir
Method Info     : Method for Landfill gases - CH4, CO2, CO, H2, N2, O2 Using Porapack N, Mol
                  Sieve, TCD - Steve Musson
```

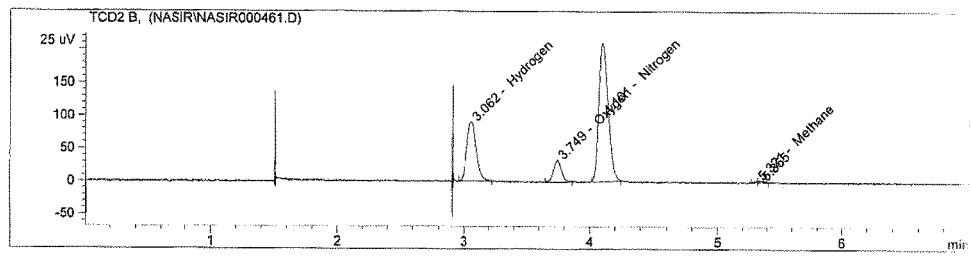

```
================================================================
                     Normalized Percent Report
================================================================

Sorted By            :     Signal
Calib. Data Modified :     Thursday, January 12, 2012 10:19:23 AM
Multiplier           :     1.0000
Dilution             :     1.0000
Use Multiplier & Dilution Factor with ISTDs Signal 1: TCD2 B, RetTime Type     Area       Amt/Area    Norm    Grp   Name
 [min]          [25 uV*s]                %
-------|------|-----------|-----------|---------|--|---------------
  2.497                         -          -          Carbon Dioxide
  3.062  BB    473.96875  4.83147e-3   3.844839       Hydrogen
  3.749  VB    147.99077  3.50659e-2   8.713023       Oxygen
  4.101  BV   1072.06763  4.84985e-2  87.296958       Nitrogen
  5.321  VV      6.49130  1.33206e-2   0.145180       Methane Totals :                             100.000000

2 Warnings or Errors :

Warning : Calibration warnings (see calibration table listing)
Warning : Calibrated compound(s) not found ================================================================
                      * End of Report *
```

Instrument 1 6/14/2013 10:53:23 AM Nasir                     Page 1 of 1

FIG. 13

```
Data File D:\DATA\NASIR\NASIR000467.D
Sample Name: NRB#4161
====================================================================
Acq. Operator   : Nasir
Acq. Instrument : Instrument 1                Location : Vial 1
Injection Date  : 14-Jun-13, 11:37:35               Inj :   1
                                             Inj Volume : Manually
Acq. Method     : C:\CHEM32\1\METHODS\LANDFILL GAS TCD MAR2011.M
Last changed    : 6/14/2013 11:36:50 AM by Nasir
Analysis Method : C:\CHEM32\1\METHODS\LANDFILL GAS TCD MAR2011.M
Last changed    : 6/14/2013 11:44:35 AM by Nasir
Method Info     : Method for Landfill gases - CH4, CO2, CO, H2, N2, O2 Using Porapack N, Mol
                  Sieve, TCD - Steve Musson
```

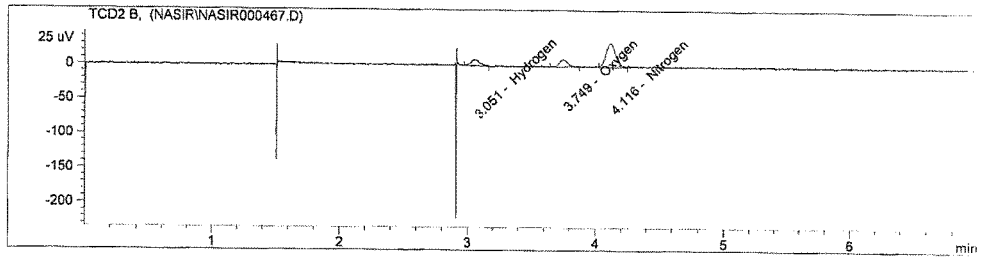

```
====================================================================
                       Normalized Percent Report
====================================================================

Sorted By             :     Signal
Calib. Data Modified  :     Thursday, January 12, 2012 10:19:23 AM
Multiplier            :     1.0000
Dilution              :     1.0000
Use Multiplier & Dilution Factor with ISTDs Signal 1: TCD2 B, RetTime Type    Area       Amt/Area      Norm    Grp   Name
  [min]       [25 uV*s]                   %
-------|------|----------|-----------|----------|--|-----------------
  2.497          -            -           -           Carbon Dioxide
  3.051 BB    42.41637   4.83147e-3    1.902551       Hydrogen
  3.749 BB    44.86104   3.50659e-2   14.604207       Oxygen
  4.116 BV   185.43852   4.84985e-2   83.493242       Nitrogen
  5.114          -            -           -           Methane Totals :                              100.000000

2 Warnings or Errors :

Warning : Calibration warnings (see calibration table listing)
Warning : Calibrated compound(s) not found ====================================================================
                          * End of Report *
```

FIG. 15

```
Data File D:\DATA\NASIR\NASIR000469.D
Sample Name: NRB#4154-2

======================================================================
Acq. Operator   : Nasir
Acq. Instrument : Instrument 1                    Location : Vial 1
Injection Date  : 14-Jun-13, 11:54:17                  Inj : 1
                                               Inj Volume : Manually
Acq. Method     : C:\CHEM32\1\METHODS\LANDFILL GAS TCD MAR2011.M
Last changed    : 6/14/2013 11:53:02 AM by Nasir
Analysis Method : C:\CHEM32\1\METHODS\LANDFILL GAS TCD MAR2011.M
Last changed    : 6/14/2013 12:01:17 PM by Nasir
Method Info     : Method for Landfill gases - CH4, CO2, CO, H2, N2, O2 Using Porapack N, Mol
                  Sieve, TCD - Steve Musson
```

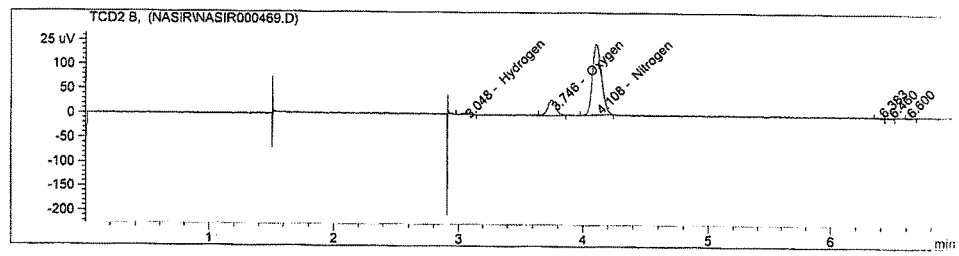

```
======================================================================
                        Normalized Percent Report
======================================================================

Sorted By            :    Signal
Calib. Data Modified :    Thursday, January 12, 2012 10:19:23 AM
Multiplier           :    1.0000
Dilution             :    1.0000
Use Multiplier & Dilution Factor with ISTDs Signal 1: TCD2 B, RetTime Type  Area       Amt/Area     Norm    Grp  Name
 [min]        [25 uV*s]                %
-------|-----|----------|-----------|----------|--|--------------------
  2.497          -           -           -          Carbon Dioxide
  3.048 BB    13.26262   4.83147e-3   0.156755      Hydrogen
  3.746 BB   144.66556   3.50659e-2  12.409786      Oxygen
  4.108 BB   736.94623   4.84985e-2  87.433458      Nitrogen
  5.114          -           -           -          Methane Totals :                              100.000000

2 Warnings or Errors :

Warning : Calibration warnings (see calibration table listing)
Warning : Calibrated compound(s) not found ======================================================================
                          * End of Report *
```

FIG. 17

Chitosan-Fe (ChFe) composite

Chitosan-Pd (ChPd) composite

Cellulose-Fe (CelluFe) composite

Cellulose-Pd (CelluPd) composite

Cellulose-Ru (CelluRu) composite

RUTHENIUM ON CHITOSAN (CHRU): CONCERTED CATALYSIS FOR WATER SPLITTING AND REDUCTION

BACKGROUND

Field of the Invention

Aspects of the invention relate generally to improved processes and catalysts to split water (i.e., to separate water into hydrogen and oxygen). The invention is particularly useful for the in situ generation of hydrogen via microwave irradiation of a ruthenium chitosan composite catalyst and the convenient reduction of nitro compounds in an aqueous medium.

Description of Related Art

Increasing energy demands and the impending global warming crisis has forced a paradigm shift in thinking towards the development of carbon-neutral, sustainable and inexpensive energy-consuming strategies. This has inspired scientists to design and develop methods for splitting water, primarily as a means for producing hydrogen (Scheme 1). The total water splitting process consists of two steps: (Step 1) proton reduction and (Step 2) water oxidation. Step 1 requires less energy compared to the key step in water splitting, i.e., water oxidation. Due to the complexity of the Step 2 reaction, the challenges in the water oxidation process involve multiple proton-coupled electron transfer processes and O—O bond formation.

$2H_2O + h\nu \rightarrow 2H_2 + O_2$ 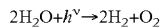

Step 1 $2H^+ + 4e^- \rightarrow H_2$ 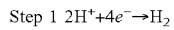

Step 2 $2H_2O \rightarrow O_2 + 4H^+ + 4e^-$ 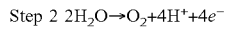

Scheme 1. Splitting of Water

There has been great effort over the years to develop a method to split water under a variety of conditions. This includes developing methods such as 1) electrolysis, 2) photoelectrochemical water splitting, 3) photocatalytic water splitting, 4) photobiological water splitting, and 5) thermal decomposition of water.

Hydrogen production from water using electrical means is not a viable option, as the energy consumed in this process is more than what is produced in the form of hydrogen. Photoelectrochemical, photocatalytic and photobiological methods are no doubt of prime importance in water splitting research. However, to date there has been very limited success due to the high complexity and cost of such methods as well as their low efficiency in producing hydrogen.

Comprehensive efforts have been made to understand the reaction mechanisms of water splitting using a catalyst. The catalytic concepts center around the use of transition metals or biological systems coupled with sunlight. However, most of the reported literature is confined to the use of conjugated complex ligands or metal oxides, and they are often designed or selected in view of their efficiency in sunlight absorption, thus mimicking nature. There has been little to no progress in the use of low-energy microwaves and non-conjugated ligands in the generation of hydrogen via water splitting.

In view of the above, there is a need to develop catalysts and reactions capable of splitting water and generating hydrogen. Accordingly, an object of the invention is to provide such a process and catalyst. Other objects will also be apparent from the detailed description of the invention.

SUMMARY OF THE INVENTION

Broadly stated, the objects of the invention are realized, according to one aspect of the invention, by synthesizing a chitosan-ruthenium catalyst and using this catalyst in a reaction to split water and produce hydrogen. There is no history of using low-energy microwaves and non-conjugated ligands in the generation of hydrogen via water splitting. In continuation of the inventors ongoing efforts to discover the versatility of renewable biopolymers as catalyst supports in organic synthesis, they serendipitously discovered in situ generation of hydrogen via water splitting using a chitosan ruthenium composite under microwave (MW) irradiation conditions. The processes of the invention also relate to the aqueous reduction of nitro compounds.

In one embodiment, the invention embraces a process for generating hydrogen and oxygen from water. The process includes the following steps: preparing a ruthenium on chitosan catalyst, bringing the catalyst into contact with an aqueous mixture under basic conditions, and applying microwave energy to the aqueous mixture to produce hydrogen and oxygen.

In one embodiment, the catalyst is prepared by a process including the following steps: suspending chitosan in water; adding $RuCl_3 \cdot 3H_2O$; adjusting the pH of the mixture to about 8.5 to about 9.5 while continuously stirring the mixture; separating the catalyst from the liquid in the mixture using a centrifuge; and drying the mixture under a vacuum. The pH of the mixture may be adjusted using ammonia, and the catalyst may be dried under a vacuum at about 30° C. to about 60° C.

In the process of separating water into hydrogen and oxygen, the aqueous mixture may be maintained at about 125° C. during the reaction. In one embodiment, the aqueous mixture is maintained at this temperature for about 30 minutes during the reaction. In another embodiment, $K_2CO_3$ is used to maintain basic conditions in the aqueous mixture.

In one embodiment of the invention, the concentration of base in the water is about 0.4 mmol/mL. In another embodiment, the microwave energy is applied at a power of about 100 watts for a time of about 60 to about 70 minutes.

In one embodiment of the invention, a nitrobenzene compound is added to the aqueous mixture prior to application of microwave energy. The nitrobenzene compound may be 4-bromo-nitrobenzene. In another embodiment of the invention, the reaction also produces a reduced organic compound. The reduced organic compound may comprise a 4-bromo-aniline.

In one embodiment of the invention, the concentration of hydrogen produced is at least 27.79%.

BRIEF DESCRIPTION OF THE DRAWINGS

The invention is more fully described by reference to the following detailed description and the accompanying drawings wherein:

FIG. 3(a) provides an SEM image of the ChRu catalyst.

FIG. 3(b) provides an X-ray diffraction image of the ChRu catalyst.

FIG. 3(c) provides an energy dispersive spectra (EDS) of ChRu catalyst.

FIG. 5 provides GS-MS data confirming the formation of diaryl either B.

FIG. 6 provides GC-MS data confirming the formation of nitro reduced diaryl either C.

FIG. 7 provides GC-MS data showing the reduction of nitro group under MW heating conditions exclusively in basic media.

FIG. 8 provides GC-MS Head Space Analysis data showing the hydrogen concentration produced with the catalyst of the invention, suspended in aqueous $K_2CO_3$, was exposed to microwave heating for 30 minutes.

FIG. 9 provides GC-MS Head Space Analysis GC-MS Head Space Analysis data showing the hydrogen concentration produced under the same conditions as in FIG. 8 but using a different base.

FIG. 10 provides GC-MS Head Space Analysis data showing the hydrogen concentration produced under the same conditions as in FIG. 8 but using a different base.

FIG. 11 provides GC-MS Head Space Analysis data showing the hydrogen concentration produced under the same conditions as in FIG. 8 but using a different base.

FIG. 12 provides GC-MS Head Space Analysis data showing the hydrogen concentration produced under the same conditions as in FIG. 8 but using a different base.

FIG. 13 provides GC-MS Head Space Analysis data showing the hydrogen concentration produced under the same conditions as in FIG. 8 but using a different base.

FIG. 15 provides GC-MS Head Space Analysis data showing the hydrogen concentration produced under the same conditions as in FIG. 8 but using a different base.

FIG. 17 provides GC-MS Head Space Analysis data showing the hydrogen concentration produced under the same conditions as in FIG. 8 but at a lower temperature (100° C. vs. 125° C.).

DETAILED DESCRIPTION OF THE INVENTION

Figure 1:
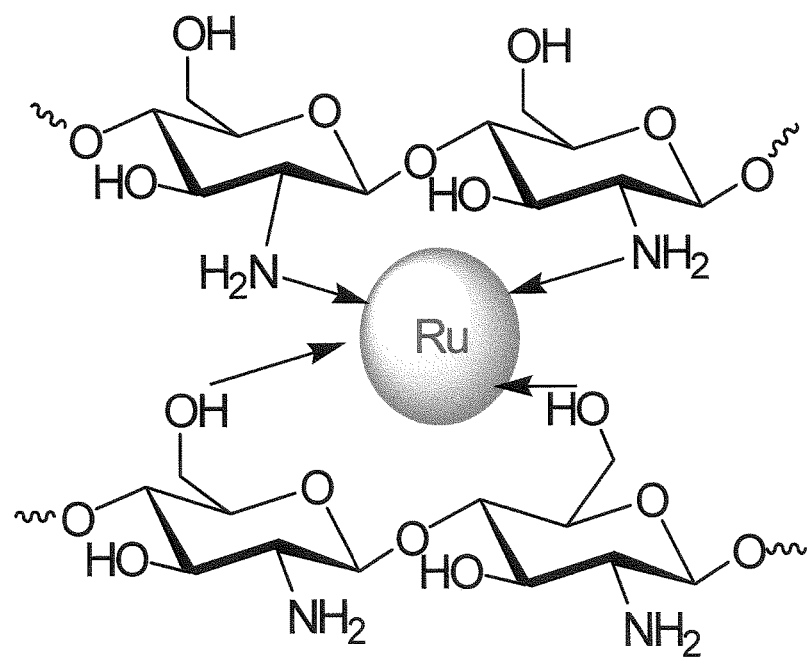
FIG. 1 is a depiction of the Chitosan-Ruthenium (Ch-Ru) composite.
Figure 3D:
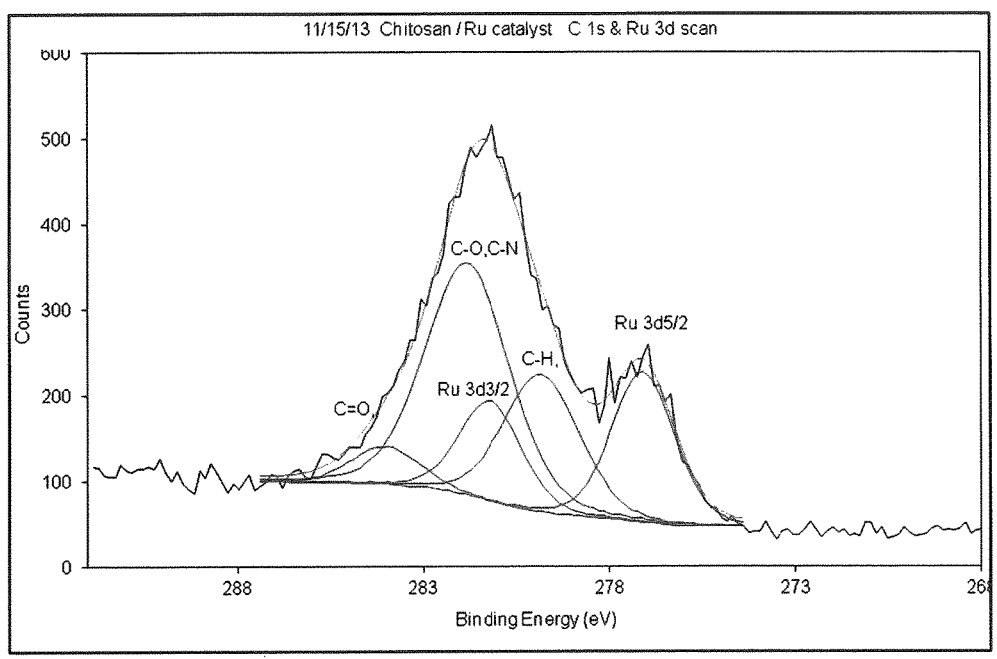
FIG. 3(d) provides XPS data for the ChRu catalyst.

Referring more specifically to the drawings, FIG. 1 is a structural representation of the Chitosan-Ru composite catalyst prepared by the inventors. The Chitosan-Ru catalyst has been characterized by SEM (FIG. 3(a)) and X-ray diffraction (XRD)(FIG. 3(b)). The signals pertaining to the Ru metal were not detected in the XRD data, possibly due to complexation with chitosan or its low percentage. However, the presence of the Ru-metal has been confirmed by energy dispersive X-ray spectroscopy (FIG. 3(c)). XPS analysis of ChRu was performed to analyze the oxidation state of the Ru metal; the binding energy peak for Ru $3d_{5/2}$ at 282.5 eV is in accordance with $Ru_{(III)}$ (XPS, FIG. 3(d)). The weight percentage of Ru was found to be 6.41% by inductively coupled plasma-atomic emission spectroscopy (ICP-AES) analysis.

Figure 4:
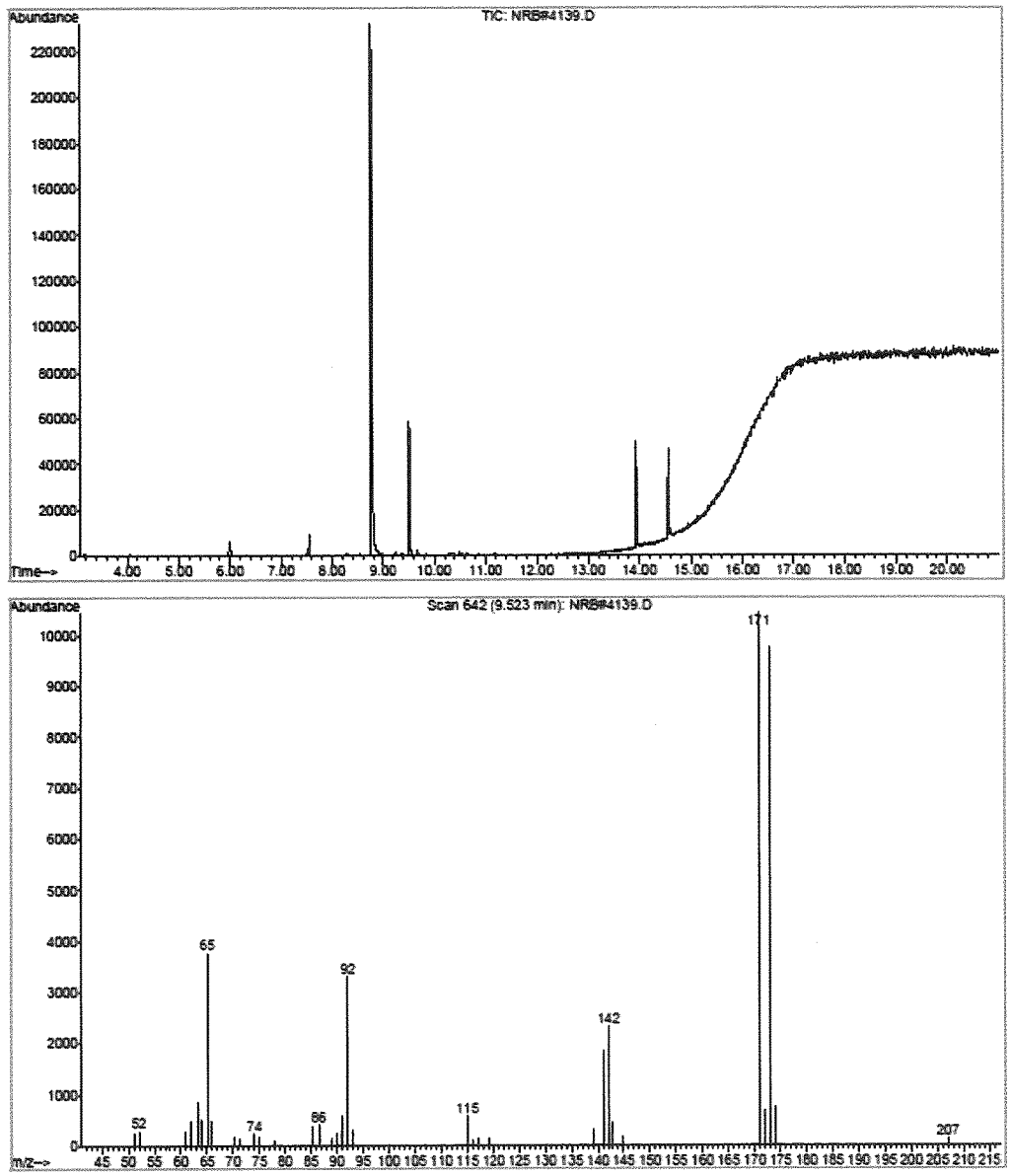
FIG. 4 provides GC-MS data confirming the formation of p-amino phenol A.

While demonstrating the application of ruthenium chitosan composite ChRu in C—O aryl bond formation in aqueous media (Scheme 2), the inventors observed the formation of three products: p-amino phenol A (FIG. 4), expected diaryl ether B (FIG. 5) and nitro reduced diaryl ether C (FIG. 6). The detection of reduced nitro group to amine in the product mixture was unexpected, which in turn prompted the inventors to investigate how the reduction of nitro group is feasible under these conditions.

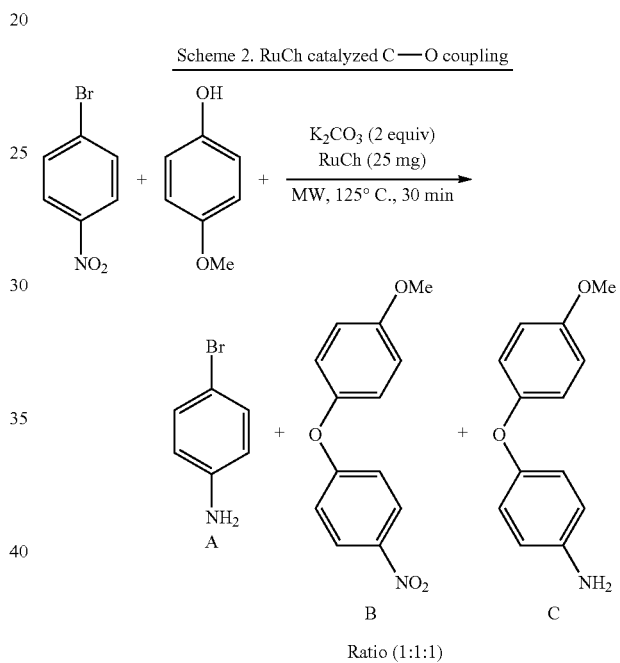

Scheme 2. RuCh catalyzed C—O coupling

Ratio (1:1:1)

The study was undertaken with 4-bromo-nitro-benzene as a model substrate in order to find out the best possible conditions for the reduction reaction. The reduction of nitro group occurs under MW heating conditions exclusively in basic media (See Table 1, FIG. 7).

TABLE 1

Screening for the catalytic reduction of nitro group

| Entry | Catalyst | Base | Temp | Product Yield[a] |
|---|---|---|---|---|
| 1 | No catalyst | — | 125° C. | 0% |
| 2 | RuCh (25 mg) | — | 125° C. | 0% |

TABLE 1-continued

| 3 | RuCh (25 mg) | $K_2CO_3$ | 125° C. | 0% |
| 4 | RuCh (25 mg) | — | 125° C./MW | 0% |
| 5 | RuChH (25 mg) | $K_2CO_3$ | 125° C./MW | 89%[b] |

Figure 2:
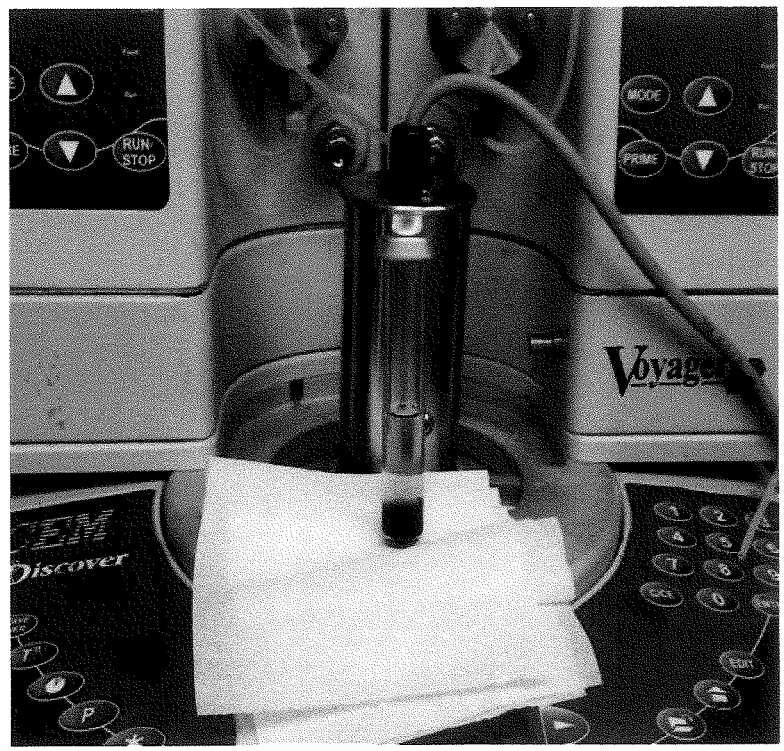
FIG. 2 shows an experimental set up to perform the MW reaction in a sealed microwave tube.

[a]Reaction condition: 4-Nitro-bromobenzene (1 mmol), RuCh-catalyst (25 mg), $K_2CO_3$ (2 mmol), Water 5 mL, MW, 125° C., 30 min; [b]GC Conversion After optimizing the reaction conditions that provided an ideal environment for reduction, the inventors searched for the source of the nitro reduction. Their studies led them to hypothesize that hydrogen may be generated in-situ in the reaction mixture, which could be responsible for the reduction of the nitro group. The hydrogen evolution through splitting of water is possible through use of a specially designed, sophisticated and highly conjugated ruthenium metal complex under photochemical conditions. In order to detect the generation of hydrogen in the reaction mixture, the inventors designed an experimental set up to perform the MW reaction in a sealed tube (see FIG. 2). The design and accompanying conditions prevent the escape of hydrogen gas. The head space analysis of the sealed tube after the reaction would help to identify the gaseous atmosphere over the reaction mixture.

Figure 14:
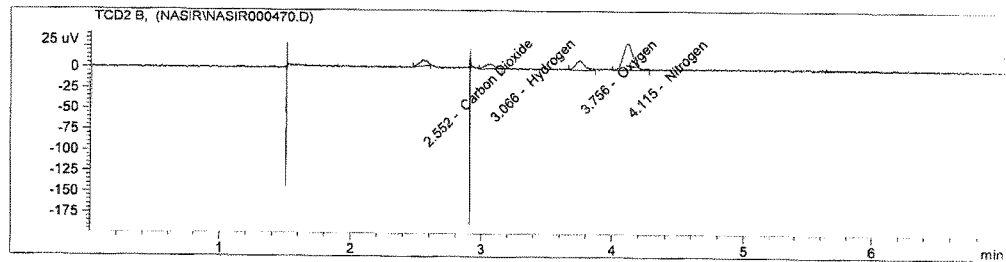
FIG. 14 provides GC-MS Head Space Analysis data showing the hydrogen concentration produced under the same conditions as in FIG. 8 but using a different base.
Figure 16:
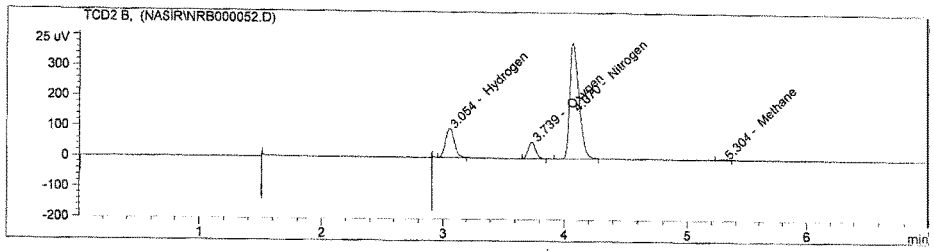
FIG. 16 provides GC-MS Head Space Analysis data showing the hydrogen concentration produced under the same conditions as in FIG. 8 using a lower concentration of $K_2CO_3$.
Figure 18:
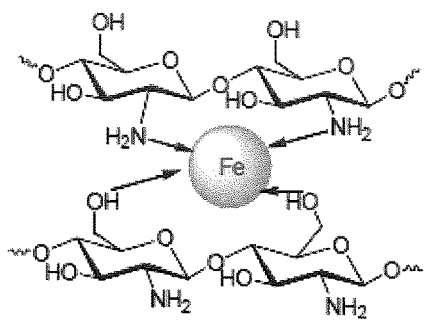
FIG. 18 is a depiction of a Chitosan-Fe (ChFe) composite.
Figure 19:
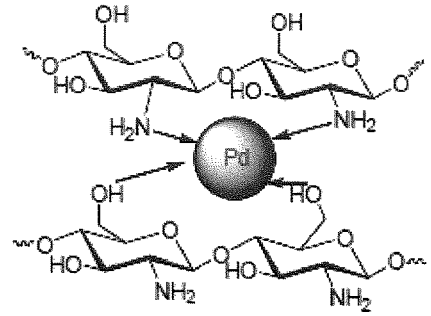
FIG. 19 is a depiction of a Chitosan-Pd (ChPd) composite.
Figure 20:
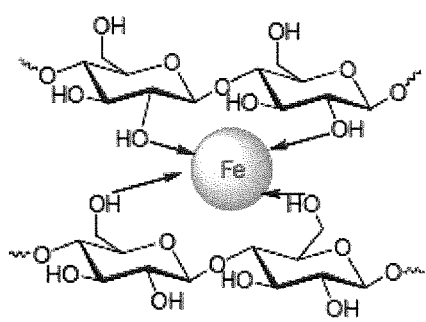
FIG. 20 is a depiction of a Cellulose-Fe (CelluFe) composite.
Figure 21:
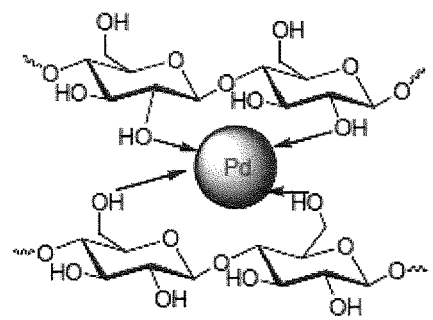
FIG. 21 is a depiction of a Cellulose-Pd (CelluPd) composite.
Figure 22:
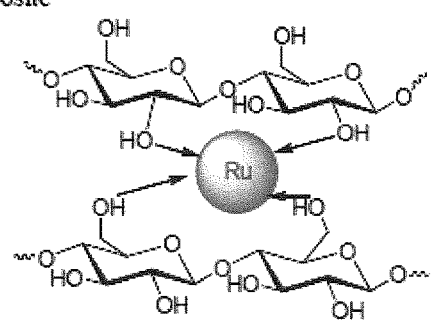
FIG. 22 is a depiction of a Cellulose-Ru (CelluRu) composite.

Accordingly, the inventors carried out experiments and studied the head space atmosphere. The head space analysis after the reaction was encouraging, as the inventors observed that substantial percentages of hydrogen were detected (~27%) (Table 2). Under neutral conditions, no splitting of water was discerned even after prolonged exposure to MW, UV-visible light and conventional heating (Table 2, entries 1-4). However, when the catalyst, suspended in aqueous $K_2CO_3$, was exposed to MW heating for 30 min, 27.79% of hydrogen (Table 2, entry 8) was detected in head space analysis (FIG. 8). The experiments were set-up to screen the different bases and their effect on water splitting. Use of $Cs_2CO_3$ as a base results in 4.15% of hydrogen (Table 2, entry 9, FIG. 9), whereas $NaHCO_3$, $Na_2CO_3$ and NaOH provided 0.79% hydrogen (Table 2, entry 10, FIG. 10), 1.22% hydrogen (Table 2, entry 11, FIG. 11) and 7.39% hydrogen (Table 2, entry 12, FIG. 12), respectively, after head space analysis. Other bases, namely KOH, $KHCO_3$ and $K_3PO_4$, generated 3.84% (Table 2, entry 13, FIG. 13), 1.28% (Table 2, entry 14, FIG. 14) and 1.90% (Table 2, entry 15, FIG. 15) of hydrogen under similar conditions. However, when the concentration of $K_2CO_3$ was reduced from 2 mmol in 5 mL water to 1 mmol in 5 mL water there was a sharp decline in the hydrogen percentage from 27.79% to 2.26% (Table 2, entry 16, FIG. 16). The MW exposure at the reduced temperature of 100° C. directly impacts the efficiency of water splitting, thereby reducing the hydrogen percentage to 0.15% (Table entry 17, FIG. 17). In basic media using $K_2CO_3$, no hydrogen was detected under conventional heating or UV-Visible light exposure (Table 2, entries 5-7). Having confirmed $K_2CO_3$ as an ideal base and its appropriate concentration for water splitting under MW, the use of alternative biorenewable support such as cellulose and other metals such as iron and palladium were explored.

TABLE 2

ChRu-catalyzed water splitting under MW

| Entry | Catalyst | Base | Time/Temp | Energy source | % Hydrogen[a] |
|---|---|---|---|---|---|
| 1 | ChRu | — | 60 min/125° C. | MW | 0% |
| 2 | ChRu | — | 24 h/ambient temp | UV | 0% |
| 3 | ChRu | — | 24 h/ambient temp | Visibile light | 0% |
| 4 | ChRu | — | 24 h/125° C. | oil bath | 0% |
| 5 | ChRu | K2CO3 | 24 h/ambient temp | UV | 0% |
| 6 | ChRu | K2CO3 | 24 h/ambient temp | Visibile light | 0% |
| 7 | ChRu | K2CO3 | 24 h/125° C. | oil bath | 0% |
| 8 | ChRu | K2CO3 | 30 min/125° C. | MW | 27.79% |
| 9 | ChRu | $Cs_2CO_3$ | 30 min/125° C. | MW | 4.15% |
| 10 | ChRu | $NaHCO_3$ | 30 min/125° C. | MW | 0.79% |
| 11 | ChRu | $Na_2CO_3$ | 30 min/125° C. | MW | 1.22% |
| 12 | ChRu | NaOH | 30 min/125° C. | MW | 7.39% |
| 13 | ChRu | KOH | 30 min/125° C. | MW | 3.84% |
| 14 | ChRu | $KHCO_3$ | 30 min/125° C. | MW | 1.28% |
| 15 | ChRu | $K_3PO_4$ | 30 min/125° C. | MW | 1.90% |
| 16[b] | ChRu | $K_2CO_3$ | 30 min/125° C. | MW | 2.26% |
| 17[c] | ChRu | $K_2CO_3$ | 30 min/100° C. | MW | 0.15% |

[a]Reaction conditions: Base (2 mmol), water (5 mL);
[b]1 mmol of $K_2CO_3$, water (5 mL), MW, 125° C.;
[c]Reaction was performed at 100° C., using 2 mmol of $K_2CO_3$ in 5 mL of water.

The microwave irradiation of ChFe, ChPd, CelluFe, CelluPd, CelluRu, (see FIGS. 18-22, respectively) under basic media, using $K_2CO_3$ as a base was performed without a detectable presence of hydrogen in the head space analysis (Table S1).

TABLE S1

Screeing of water splitting using Fe, Pd and alternative biopolymer

| Entry | Catalyst | Base | Time/Temp | Energy source | Hydrogen[a,b] |
|---|---|---|---|---|---|
| 1 | CelluRu | $K_2CO_3$ | 30 min/125° C. | Microwave | 0.00% |
| 2 | CelluPd (II) | $K_2CO_3$ | 30 min/125° C. | Microwave | 0.00% |
| 3 | CelluFe(III) | $K_2CO_3$ | 30 min/125° C. | Microwave | 0.00% |
| 4 | ChFe(III) | $K_2CO_3$ | 30 min/125° C. | Microwave | 0.00% |
| 5 | ChPd (II) | $K_2CO_3$ | 30 min/125° C. | Microwave | 0.00% |

[a]Reaction condition: $K_2CO_3$ (2 mmol), Water (5 mL), MW, Metal catalyst (25 mg).
[b]Percentage after Head space analysis

TABLE S2

Recycling of ChRu catalyst in nitro reduction

| Entry | Substrate | Time | Product | Conversion[a],[b] |
|---|---|---|---|---|
| Cycle 1 | 4-Br-C6H4-NO2 | 60 min | 4-Br-C6H4-NH2 | >99% |
| Cycle 2 | 4-Br-C6H4-NO2 | 60 min | 4-Br-C6H4-NH2 | >99% |
| Cycle 3 | 4-Br-C6H4-NO2 | 60 min | 4-Br-C6H4-NH2 | >99% |
| Cycle 4 | 4-Br-C6H4-NO2 | 60 min | 4-Br-C6H4-NH2 | >99% |
| Cycle 5 | 4-Br-C6H4-NO2 | 60 min | 4-Br-C6H4-NH2 | >99% |

[a]Reaction condition: 1 mmol of 4-nitro bromobenzene, 2 mmol of $K_2CO_3$, ChRu (25 mg), 5 mL water, MW, 125° C., 60 min; [b]GC conversion Scheme 3. Metal-catalyzed reduction of nitro group

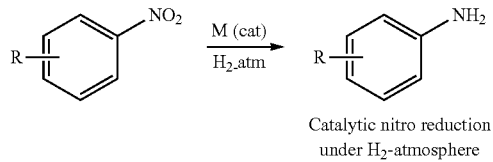

Catalytic nitro reduction under $H_2$-atmosphere

M = Metal
M = Pd, Pt, Ni, Ru etc

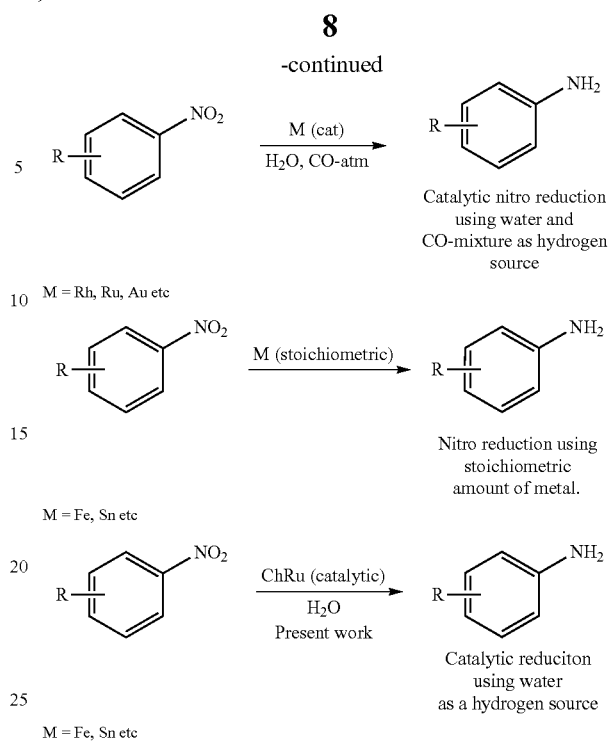

Catalytic nitro reduction using water and CO-mixture as hydrogen source

M = Rh, Ru, Au etc

Nitro reduction using stoichiometric amount of metal.

M = Fe, Sn etc

ChRu (catalytic)
$H_2O$
Present work

Catalytic reduciton using water as a hydrogen source

M = Fe, Sn etc

The selective reduction of nitro compounds to amines is one of the very important transformations in organic synthesis, and consequently there are number of procedures for the reduction of nitro compounds (Scheme 3). Due to concern for the environment, the search for simple, chemoselective, affordable and environmentally benign methods that avoid the use of hazardous and expensive reducing agents in stoichiometric amounts has gained prime importance. The use of a binary mixture of CO and $H_2O$ as a hydrogen source along with specially designed Rh, Au or Ru metal complex catalysts has been considered as one of the most useful methods for nitro reduction. The in-situ generation of hydrogen from water and its utilization in reduction of nitro compounds using simple biodegradable renewable chitosan has never been reported (see bottom, Scheme 3).

TABLE 3

ChRu catalyzed reduction of nitro compund.

| Entry | Substrate | Time | Product | Conversion[a],[b] |
|---|---|---|---|---|
| 1 | C6H5-NO2 | 60 min | C6H5-NH2 | >99% |
| 2 | 4-Br-C6H4-NO2 | 60 min | 4-Br-C6H4-NH2 | >99% |
| 3 | 4-I-C6H4-NO2 | 60 min | 4-I-C6H4-NH2 | >99% |

TABLE 3-continued

ChRu catalyzed reduction of nitro compund.

| Entry | Substrate | Time | Product | Conversion[a],[b] |
|---|---|---|---|---|
| 4 | 4-methyl-nitrobenzene | 70 min | 4-methyl-aniline | >99% |
| 5 | 4-methoxy-nitrobenzene (MeO) | 70 min | 4-methoxy-aniline (MeO) | >99% |
| 6 | methyl 4-nitrobenzoate (MeOOC) | 60 min | methyl 4-aminobenzoate (MeOOC) | >99% |

[a]Reaction condition: 1 mmol of nitro compound, 2 mmol of $K_2CO_3$, ChRu (25 mg), 5 mL water, MW, 125° C., 60-70 min; [b]GC conversion The experimental procedure entailed placing aromatic nitro compound (1 mmol) into a microwave reaction tube, to which $K_2CO_3$ (2 mmol), ChRu (25 mg) and 5 mL of water were added and exposed to microwave irradiation for 60-70 min at 125° C. The reaction was monitored using GCMS. In almost all the cases, the nitro group is selectively reduced to the corresponding amine (Table 3).

The recovery of the catalyst is the most important goal in a sustainable organic synthesis. In industrial application of heterogeneous system, the lifetime of the catalyst and its level of reusability are significantly important factors. To demonstrate recyclability of ruthenium chitosan composite, a set of experiments was conducted for the hydrogenation of 4-nitro bromo benzene using the recycled ChRu catalyst. After the completion of the reaction, the catalyst was recovered, washed with acetone, and dried under vacuum. A fresh reaction was then set-up using fresh reactants and recycled catalyst and subjected to MW irradiation. The ChRu catalyst could be used at least five times without any change in its activity. Metal leaching was studied using ICP-AES analysis of the catalyst before and after the completion of the reaction. The Ru concentration was found to be 6.41% before the reaction and 6.35% after the reaction. The very small amount of Ru metal was detected in the aqueous mixture. The negligible amount of Ru leaching may be due to the well-defined structure of chitosan with its abundance of amine and hydroxyl functional groups. While it is only theory, chitosan's advantageous structural characteristics may result in Ru chelating via non-covalent interaction.

Examples

Experimental Procedure for Synthesis of Chitosan Ruthenium Catalyst (ChRu)

The Ruthenium on Chitosan catalyst was made as follows. Chitosan (3 g, medium molecular weight, Aldrich, CSA #9012-76-4) was suspended in 100 mL of water. To this suspension, 500 mg of $RuCl_3 \cdot 3H_2O$ was added. The pH was adjusted to 9 using 25% ammonia, and the suspension was continuously stirred overnight. The catalyst was separated using a centrifuge operated at 5000 rpm for 5 minutes. The catalyst was then dried under vacuum at 50° C. for about 2 hours to about 3 hours.

Reduction of Nitro Group

Nitro compound (e.g., the aromatic nitro compound, 4-bromonitrobenzene, 1.0 mmol), ChRu (25 mg, 0.015, mol %) and $K_2CO_3$ (2 mmol) were placed in a crimp-sealed thick-walled glass tube equipped with a pressure sensor and a magnetic stirrer. Water (5 mL) was added to the reaction mixture. The reaction tube was placed inside the cavity of a CEM Discover focused microwave synthesis system and operated at 125° C. (temperature monitored by a built-in infrared sensor) and 100 Watts for 60-70 minutes. After completion of the reaction, the catalyst was removed from the reaction mixture using a centrifuge. Reduction of the nitro group has been monitored using GCMS. The clear liquid was cooled slowly, and, in most cases, an analytically pure sample of corresponding amine was obtained. The samples can be isolated from the water medium by simple decantation.

Figure 23:
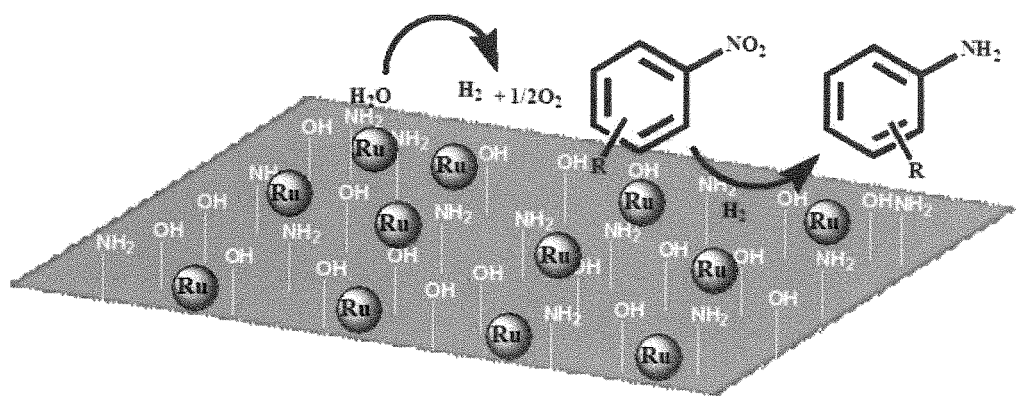
FIG. 23 is a depiction of water splitting and nitro compound reduction reactions on a Chitosan-Ruthenium (ChRu) composite catalyst.

In brief, the inventors have demonstrated the unprecedented use of pure water as a hydrogen source in the catalytic hydrogenation of nitro compounds wherein ruthenium chitosan composite can split water under microwave irradiation conditions. See FIG. 23. Ruthenium chitosan composite performs a dual action of producing hydrogen and subsequently catalyzing the reduction of nitro groups to amine under MW irradiation. As a result of this invention, low energy MW has been shown to assist in weakening the O—H bound in water molecules, which results in instigating the splitting of water into hydrogen. These findings may pave the way for the future the expansion of microwave-assisted chemistry in concerted reactions such as hydrogen production from water and hydrogenation.

As the present invention may be embodied in several forms without departing from the spirit or essential characteristics thereof, it will be understood that the invention is not limited by the details of the foregoing description, unless otherwise specified, but rather should be construed broadly within its spirit and scope as defined in the appended claims, and therefore all changes and modifications that fall within the metes and bounds of the claims. Accordingly, the invention is defined by the appended claims.

REFERENCES

[1]. R. E. Blankenship, *Molecular Mechanisms of Photosynthesis*, Blackwell Science, Oxford, U.K., 2002.

[2]. H. J. Lewerenz, L. Peter, *Photoelectrochemical Water Splitting: Materials, Processes and Architectures*, The Royal Society of Chemistry 2013.
[3]. R. V. D. Krol, M. Gratzel, *Photoelectrochemical Hydrogen Production*, Springer Science, 2012.
[4]. T. Hisatomi, J. Kubota, K. Domen, *Chem. Soc. Rev.*, 2014, DOI: 10.1039/C3CS60378D
[5]. A. Kudo, Y. Miseki, *Chem. Soc. Rev.*, 2009, 38, 253-278.
[6]. J. J. Concepcion, J. W. Jurss, M. K. Brennaman, P. G. Hoertz, A. O. T. Patrocinio, N. Y. Murakami, J. L. Templeton, T. J. Meyer, *Acc. Chem. Res.* 2009, 42, 1954-1965.
[7]. S. Romain, L. Vigara, A. Llobet, *Acc. Chem. Res.* 2009, 42, 1944-1953.
[8]. G. S. Parkinson, Z. Novotny, P. Jacobson, M. Schmid, U. Diebold, *J. Am. Chem. Soc.*, 2011, 133, 12650-12655.
[9]. R. H. Gonçalves, B. H. R. Lima, E. R. Leite, *J. Am. Chem. Soc.*, 2011, 133, 6012-6019.
[10]. M. Higashi, K. Domen, R. Abe, *J. Am. Chem. Soc.*, 2012, 134, 6968-6971.
[11]. M. T. Mayer, C. Du, D. Wang, *J. Am. Chem. Soc.*, 2012, 134, 12406-12409.
[12]. J. Cohen, K. Kim, M. L. Ghirardi, K. Schulten, M. Seibert, P. King, *Biochem. Soc. Trans.* 2005, 33, 80-82.
[13]. A. S. Fedorov, S. Kosourov, M. Seibert, M. L. Ghirardi, *Appl. Biochem. Biotechnol.* 2005, 403-412.
[14]. G. Sirasani, L. Tong, and E. P. Balskus, *Angew. Chem. Int. Ed.* 2014, 53, 7785-7788
[15]. L. Vigh, D. A. Los, I. Horv_th, N. Murata, *Proc. Natl. Acad. Sci.* USA 1993, 90, 9090-9094.
[16]. X. H. Li, X. Wang, M. Antonietti, *Chem. Sci.*, 2012, 3, 2170
[17]. K. S. Joya, Y. F. Joya, K. Ocakoglu, R. V. Krol, *Angew. Chem. Int. Ed.* 2013, 52, 10426-10437.
[18]. R. B. Nasir Baig, R. S. Varma *Chem. Commun.*, 2013, 49, 752-770.
[19]. R. B. Nasir Baig, B. R. Vaddula, M. A. Gonzalez, R. S. Varma, *RSC Adv.*, 2014, 4, 9103-9106.
[20]. R. B. Nasir Baig, M. N. Nadagouda, R. S. Varma, *Green Chem.*, 2014, 16, 2122-2127.
[21]. X. Yang, M. B. Hall, *J. Am. Chem. Soc.*, 2010, 132, 120-130
[22]. M. J. Krische, Y. Sun, *Acc. Chem. Res.*, 2007, 40, 1237-1237.
[23]. I. Sorribes, G. Wienhcfer, C. Vicent, K. Junge, Rosa Lusar, M. Beller, *Angew. Chem. Int. Ed.* 2012, 51, 7794-7798.
[24]. D. Cantillo, M. Baghbanzadeh, C. O. Kappe, *Angew. Chem. Int. Ed.* 2012, 51, 10190-10193.
[25]. L. He, L. C. Wang, H. Sun, J. Ni, Y. Cao, H. Y. He, K. N. Fan, *Angew. Chem. Int. Ed.* 2009, 48, 9538-9541.
[26]. C. O. Kappe, *Angew. Chem. Int. Ed.* 2013, 52, 2-7
[27]. G. B. Dudley, A. E. Stiegman, M. R. Rosana, *Angew. Chem. Int. Ed.* 2013, 52, 2-8.

The invention claimed is:

1. A process for generating hydrogen and oxygen from water, the process comprising preparing a ruthenium on chitosan catalyst, bringing the catalyst into contact with an aqueous mixture under basic conditions, and applying microwave energy to the aqueous mixture to produce hydrogen and oxygen.

2. The process of claim 1 wherein the catalyst is prepared by
   (a) suspending chitosan in water;
   (b) adding $RuCl_3 \cdot 3H_2O$;
   (c) adjusting the pH of the mixture to about 8.5-9.5 while continuously stirring the mixture;
   (d) separating the catalyst from the liquid in the mixture; and
   (e) drying the mixture under a vacuum.

3. The process of claim 2 wherein the pH of the mixture is adjusted using ammonia.

4. The process of claim 2 wherein the catalyst is dried under a vacuum at a temperature from about 30-60° C.

5. The process of claim 2 wherein the catalyst is separated from the liquid in the mixture using a centrifuge.

6. The process of claim 1 wherein aqueous mixture is maintained at about 125° C. during the reaction.

7. The process of claim 6 wherein the aqueous mixture is maintained at about 125° C. for about 30 minutes during the reaction.

8. The process of claim 1 wherein $K_2CO_3$ is used to maintain basic conditions in the aqueous mixture.

9. The process of claim 1 wherein the concentration of base in the water is about 0.4 mmol/mL.

10. The process of claim 1 wherein microwave energy is applied at a power of about 100 watts for a time of about 60 to about 70 minutes.

11. The process of claim 1 wherein a nitrobenzene compound is added to the aqueous mixture prior to application of microwave energy.

12. The process of claim 11 wherein the nitrobenzene compound is 4-bromo-nitrobenzene.

13. The process of claim 12 wherein the reaction also produces a reduced organic compound.

14. The process of claim 13 wherein the reduced organic compound comprises a 4-bromo-aniline.

15. The process of claim 1 wherein the concentration of hydrogen produced is at least 4.15%.

16. The process of claim 1 wherein the concentration of hydrogen produced is at least 27.79%.

* * * * *